(12) United States Patent
Saito et al.

(10) Patent No.: US 6,198,954 B1
(45) Date of Patent: Mar. 6, 2001

(54) URINE SUGAR DETECTING DEVICE AND METHOD OF FABRICATING THE SAME

(75) Inventors: Atsushi Saito; Soichi Saito, both of Tokyo (JP)

(73) Assignee: NEC Corporation, Tokyo (JP)

(*) Notice: Subject to any disclaimer, the term of this patent is extended or adjusted under 35 U.S.C. 154(b) by 0 days.

(21) Appl. No.: 09/268,996

(22) Filed: Mar. 16, 1999

(30) Foreign Application Priority Data

Mar. 20, 1998 (JP) ................................................ 10-072077

(51) Int. Cl.$^7$ ...................................................... A61B 5/05

(52) U.S. Cl. ......................... 600/345; 600/347; 600/361; 600/365

(58) Field of Search ..................................... 600/345, 348, 600/347, 361, 365, 364, 573

(56) References Cited

U.S. PATENT DOCUMENTS

| 5,730,149 | * | 3/1998 | Nakayama et al. | 600/573 |
| 5,820,551 | * | 10/1998 | Hill et al. | 600/345 |
| 6,021,339 | * | 2/2000 | Saito et al. | 600/345 |

* cited by examiner

*Primary Examiner*—Cary O'Connor
*Assistant Examiner*—Michael Astorino
(74) *Attorney, Agent, or Firm*—Young & Thompson

(57) ABSTRACT

A urine sugar detecting device including (a) a urine sugar sensor including a contact electrode and a cover film covering the contact electrode therewith, (b) a cartridge encasing the urine sugar sensor in fluid tight except the contact electrode, and (c) at least one contact pin having a straightly extending proximal portion and an obliquely, downwardly inclining distal portion, the contact pin being kept deformed in the cartridge so as to have a force with which the contact pin pierces the cover film to thereby have electrical connection with the contact electrode.

8 Claims, 6 Drawing Sheets

URINE SUGAR DETECTING DEVICE AND METHOD OF FABRICATING THE SAME

BACKGROUND OF THE INVENTION

1. Field of the Invention

The invention relates to a urine sugar detecting device, and a method of fabricating the same.

2. Description of the Related Art

Many urine sugar detecting devices have been suggested so far. For instance, Japanese Unexamined Patent Publication No. 8-193969 has suggested a device for electrically, chemically detecting glucose, and Japanese Patent Publication No. 8-23545 has suggested an enzyme electrode to be used for a glucose sensor.

For another instance, Japanese Unexamined Patent Publication 5-72172 has suggested an enzyme electrode to be used for a urine sugar detecting sensor. FIG. 1 illustrates the enzyme electrode suggested in the Publication. The illustrated enzyme electrode is fabricated as follows.

First, a platinum layer is formed on an insulating substrate 1 by sputtering. Then, the platinum layer is patterned by photolithography and etching steps to thereby form operation electrodes and reference electrodes. Each of the operation and reference electrodes is comprised of a sensitive portion 2a, a lead portion (not illustrated), and a connection portion 2b.

Then, dip coating is applied to the insulating substrate 1 to thereby form an enzyme film 3 over the insulating substrate 1 except the connection portions 2b. Thereafter, the insulating substrate 1 is divided into enzyme electrodes.

In the enzyme electrode illustrated in FIG. 1, dip coating is applied to the insulating substrate 1 in order to form the enzyme film 3. However, the dip coating is accompanied with problems that the dip coating cannot be applied to a plurality of substrates at a time, and hence, is not suitable for mass-production of enzyme electrodes, and that it is quite difficult for the dip coating to uniformize film quality and film thickness.

To solve these problems, Japanese Patent Publication No. 8-16669 has suggested a method of patterning an enzyme film in a region other than contact electrodes by photolithography. In this method, lift-off is carried out using a photoresist film. This method is carried out as follows.

First, contact electrodes are formed on a substrate. Then, a photoresist film is formed over the substrate by spin coating. Then, the photoresist film is removed in a region other than contact electrodes by photolithography.

Then, an enzyme film is formed over the substrate by spin coating. Then, the residual photoresist film is dissolved by organic solvent to thereby remove the enzyme film on the contact electrodes.

According to the method suggested in Japanese Patent Publication No. 8-16669, a plurality of substrates can be treated at a time, because a photoresist film can be applied to those substrates at a time by spin coating. Hence, the suggested method is suitable for mass-production of enzyme electrodes, and, in addition, has an advantage that film quality and film thickness can be readily uniformized.

However, the method suggested in Japanese Patent Publication No. 8-16669 needs to carry out a photolithography step. In other words, the method needs a particular apparatus for carrying out photolithography, and hence, is accompanied with a problem that it is not possible to shorten a time for fabricating an enzyme electrode.

In addition, the necessity of preparing a photolithography apparatus increases fabrication costs.

SUMMARY OF THE INVENTION

In view of the above-mentioned problems, it is an object of the present invention to provide a urine sugar detecting device which can be fabricated in simpler fabrication steps, specifically, without carrying out a photolithography step. It is also an object of the present invention to provide a method of fabricating such a urine sugar detecting device.

In one aspect of the present invention, there is provided a urine sugar detecting device including (a) a urine sugar sensor including at least one contact electrode and a cover film covering the contact electrode therewith, (b) a cartridge encasing the urine sugar sensor in fluid tight except the contact electrode, and (c) at least one contact pin encased in the cartridge and electrically connecting the contact electrode through the cover film.

It is preferable that the contact pin pierces the cover film to thereby have electrical connection with the contact electrode. For instance, the contact pin is kept deformed in the cartridge so as to have a force with which the contact pin pierces the cover film.

For instance, the contact pin is comprised of a straightly extending proximal portion and an obliquely, downwardly inclining distal portion, in which case, it is preferable that the distal portion obliquely, downwardly inclines by about 45 degrees.

In another aspect of the present invention, there is provided a method of fabricating a urine sugar detecting device, including the steps of (a) fixing a urine sugar sensor in a lower half of a cartridge, the sensor including a contact electrode and a cover film covering the contact electrode therewith, (b) fixing a contact pin in an upper half of a cartridge, the contact pin having a free distal end, and (c) coupling the lower and upper halves of a cartridge in fluid tight so that the distal end of the contact pin pierces the cover film, and makes electrical contact with the contact electrode.

There is further provided a method of fabricating a urine sugar detecting device, including the steps of (a) fixing a urine sugar sensor in a lower half of a cartridge, the urine sugar sensor including a contact electrode and a cover film covering the contact electrode therewith, (b) fixing a contact pin in an upper half of a cartridge so that a straightly extending proximal portion of the contact pin is fixed and an obliquely, downwardly inclining distal portion of the contact pin is free, and (c) coupling the lower and upper halves of a cartridge in fluid tight so that the distal portion of the contact pin is deformed to thereby pierce the cover film, and makes electrical contact with the contact electrode.

A urine sugar detecting device is generally fabricated as follows. First, contact electrodes composed of platinum and silver are formed on an insulating substrate. Then, an organic, insulating thin film for detecting glucose is formed over the insulating substrate. According to this method, it is impossible to externally establish electrical connection, because the insulating thin film entirely covers the contact electrodes therewith.

Hence, in the present invention, a contact pin is pressurized to thereby pierce the insulating thin film at a distal end thereof. As a result, the contact pin makes electrical connection with the contact electrodes to thereby establish electrical connection.

In accordance with the present invention, it no longer necessary to carry out a step of removing the insulating thin film formed on the contact electrodes, and a step of forming the insulating thin film on the substrate in an area other than terminals. Hence, the urine sugar detecting device can be fabricated in simplified process relative to a conventional process.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

A urine sugar detecting device in accordance with a preferred embodiment of the invention is used for measuring a concentration of glucose contained in urine, and basically includes a urine sugar detecting sensor 1 and a cartridge 10 encasing the urine sugar sensor therein. In the cartridge 10, the urine sugar detecting sensor 1 is electrically connected to a circuit for detecting a glucose concentration. The cartridge 10 is formed fluid tight, because the urine sugar detecting device is dipped into urine when a glucose concentration is to be detected.

Figure 1:
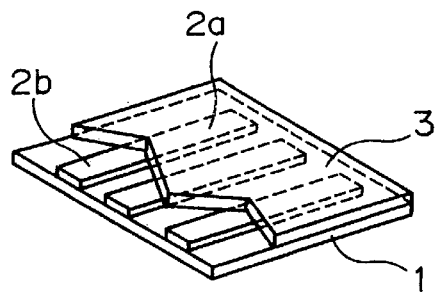
FIG. 1 is a perspective view of an enzyme electrode to be used in a conventional urine sugar detecting device.
Figure 2:
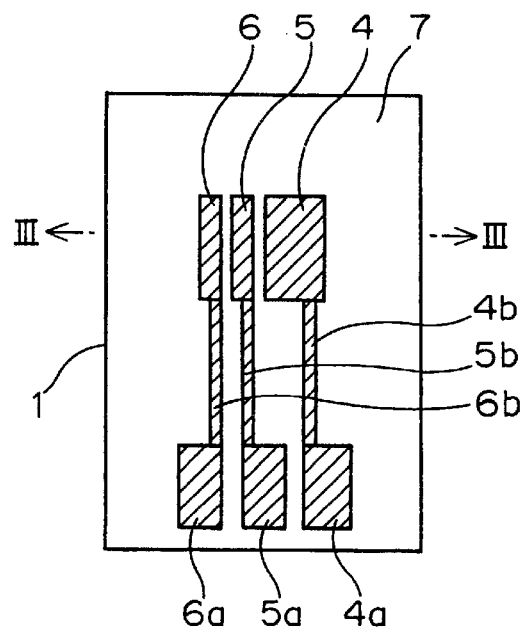
FIG. 2 is a plan view illustrating a urine sugar detecting sensor in a urine sugar detecting device in accordance with an embodiment of the present invention.
Figure 3:
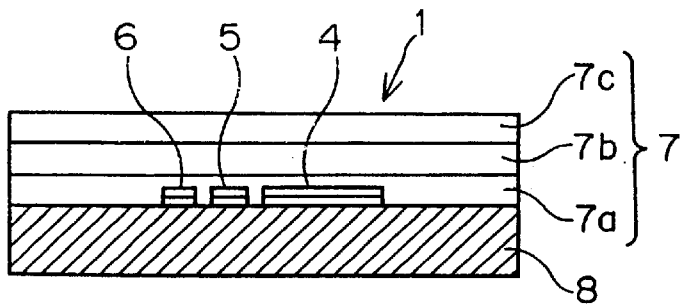
FIG. 3 is a cross-sectional view taken along the line III—III in FIG. 2.

As illustrated in FIGS. 2 and 3, the urine sugar detecting sensor 1 is comprised of an insulating substrate 8, an operation electrode 4, an opposing electrode 5, a reference electrode 6, contact electrodes 4a, 5a and 6a, leads 4b, 5b and 6b, and a film 7 for detecting glucose.

The insulating substrate 8 is a silicon substrate on which a silicon dioxide film is formed. As an alternative, the insulating substrate 8 may be composed of glass, quartz, polyimide, polycarbonate, or glass epoxy.

The electrodes 4, 5, and 6, the contact electrodes 4a, 5a and 6a, and the leads 4b, 5b and 6b are all formed on the insulating substrate 8. The leads 4b, 5b and 6b electrically connect the operation electrode 4, the opposing electrode 5, and the reference electrode 6 to the contact electrodes 4a, 5a and 6a, respectively. The operation electrode 4, the opposing electrode 5, and the reference electrode 6 cooperate with one another to thereby measure a concentration of hydrogen peroxide contained in urine.

The operation electrode 4 and the opposing electrode 5 are comprised of a titanium layer and a platinum layer deposited on the titanium layer. As an alternative, the operation electrode 4 and the opposing electrode 5 may be composed of platinum and any one of carbon, gold, and iridium. The operation electrode 4 and the opposing electrode 5 may be formed by evaporation, sputtering, screen printing, or plating. When the operation electrode 4 and the opposing electrode 5 are formed by sputtering, it is preferable that the titanium layer has a thickness in the range of 0.02 to 0.2 μm, and the platinum layer has a thickness in the range of 0.1 to 1.0 μm.

The reference electrode 6 is comprised of a silver layer formed on the insulating substrate 8, and a silver chloride layer formed by chemically treating a surface of the silver layer. A titanium layer and a platinum layer may be formed under the silver layer in order to enhance adhesion. When the reference electrode 6 is formed by sputtering, it is preferable that the silver layer has a thickness in the range of 0.1 to 1.0 μm. The silver chloride layer may be formed by treating a surface of the silver layer with iron chloride (II) solution or chromium chloride (II) solution, or by electrolyzing the silver layer in chloride solution.

The operation electrode 4 has a size of 1.2 mm×2.0 mm, the opposing electrode 5 has a size of 0.4 mm×2.0 mm, and the reference electrode 6 has a size of 0.4 mm×2.0 mm. The leads 4b, 5b and 6b have the same size of 1.2 mm×2.8 mm. The contact electrodes 4a, 6a and 6a have the same size of 1.6 mm×0.8 mm. The urine sugar sensor 1 has a size of 6.0 mm×9.0 mm.

As illustrated in FIG. 3, the electrodes 4, 5, and 6, the contact electrodes 4a, 5a and 6a, and the leads 4b, 5b and 6b are all covered with the glucose detecting film 7. The glucose detecting film 7 contains glucose oxidase (GOD) therein. The glucose detecting film 7 has a multi-layered structure including a first film 7a formed on the insulating substrate 8, a second film 7b formed on the first film 7a, and a third film 7c formed on the second film 7b.

The first film 7a allows only hydrogen peroxide to pass therethrough, and disallows interfering substance to pass therethrough. As a result, the first film 7a removes interfering substance. The first film 7a is composed of at least one of silane coupling agent, fluorine contained resin, and acetyl cellulose. The first film 7a is formed by spin coating.

The second film 7b fixes enzyme therein. The second film 7b is formed by spin-coating an aqueous solution containing glucose, albumin, and glutaric aldehyde.

The third film 7c restricts transmission of glucose therethrough to hereby broaden a range in which the urine sugar detecting device can detect glucose. The third film 7c is formed by spin-coating any one of silicone, carboxymethyl cellulose, polyurethane, perfluorocarbon.

A total thickness of the first to third films 7a to 7c is designed to be equal to or smaller than 1 μm.

Glucose oxidase oxidizes glucose to δ-D-gluconic lactone. With this oxidation, oxygen is reduced to hydrogen peroxide in accordance with the following reaction formula.

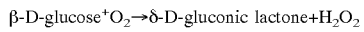

The thus generated hydrogen peroxide is oxidized on the electrodes 4, 5 and 6, and an oxidation current is measured in the oxidation. Based on the thus measured oxidation current, a concentration of hydrogen peroxide can be detected in accordance with the following reaction formula.

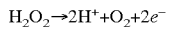

Since a hydrogen peroxide concentration is in proportion to a glucose concentration, a glucose concentration can be calculated based on the hydrogen peroxide concentration.

With reference to FIG. 2, a constant voltage in the range of 0.4V to 0.7V is applied across the operation electrode 4 and the reference electrode 6 in the urine sugar sensor 1. As a result, hydrogen peroxide is anodically oxidized on the operation electrode 4, and an oxidation current runs between the operation electrode 4 and the opposing electrode 5. The thus generated oxidation current is measured, and a hydrogen peroxide concentration is detected in the above-mentioned manner.

Hereinbelow is explained a method of fabricating the above-mentioned urine sugar sensor 1.

First, a titanium layer and a platinum layer are formed on an insulating substrate 8 having a size of 60 mm×70 mm by sputtering. Further, a silver layer is formed over the platinum layer by sputtering. Then, the titanium, platinum and silver layers are patterned by photolithography into the operation electrode 4, the opposing electrode 5, the reference electrode 6, the leads 4b, 5b and 6b, and the contact electrodes 4a, 5a and 6a.

Then, the resultant product is treated with iron chloride (III) solution to thereby form a silver chloride layer at a surface of the silver layer.

Then, the first, second and third films 7a, 7b and 7c are formed in this order on the insulating substrate 8 by spin-coating.

Then, the insulating substrate 8 is divided into separate urine sugar detecting sensors 1 each having a size of 6 mm×9 mm. Each of the urine sugar detecting sensors 1 is encased into the cartridge 10. Thus, there is completed a urine sugar detecting device.

Figure 4A:
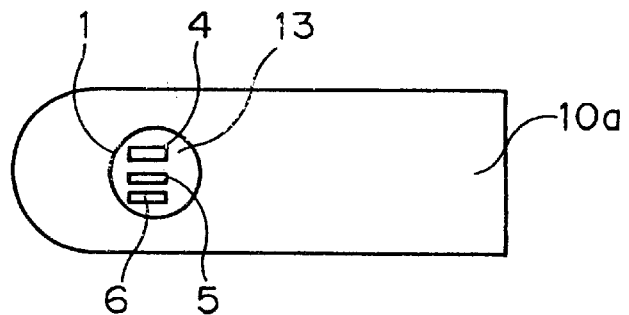
FIG. 4A is a plan view of a urine sugar detecting sensor in accordance with an embodiment of the present invention. 10
Figure 4B:
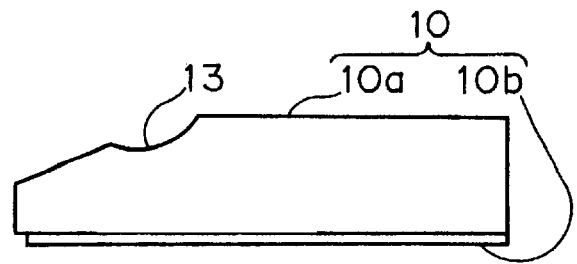
FIG. 4B is a side view of the urine sugar detecting sensor illustrated in FIG. 4A.
Figure 5A:
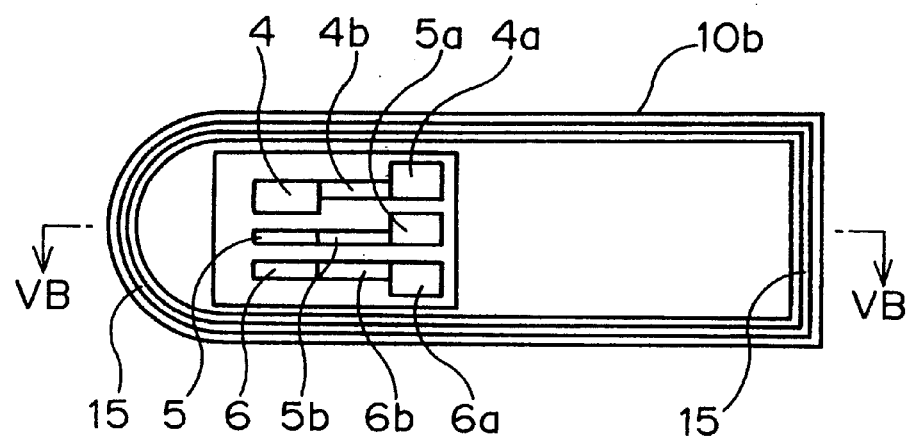
FIG. 5A is a plan view of a lower half of a cartridge constituting a urine sugar detecting sensor in accordance with the embodiment.
Figure 5B:
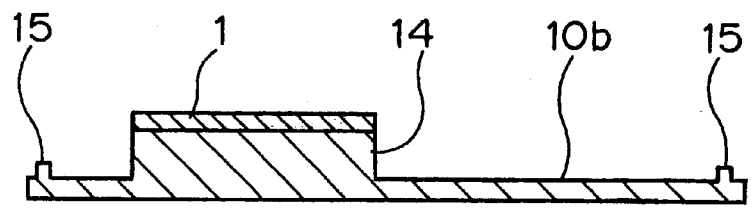
FIG. 5B is a cross-sectional view taken along the line VB—VB in FIG. 5A.
Figure 6A:
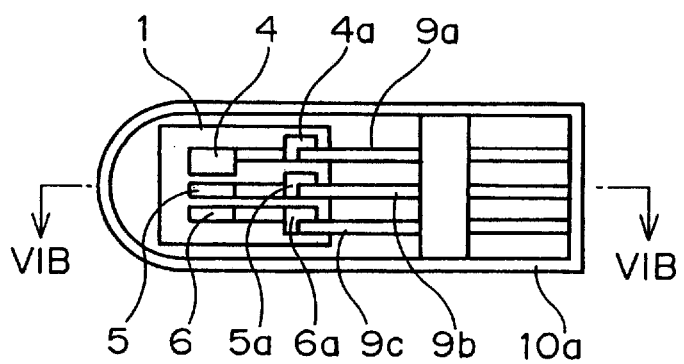
FIG. 6A is a longitudinal cross-sectional view illustrating an inside of a detecting sensor in accordance with the embodiment.
Figure 6B:
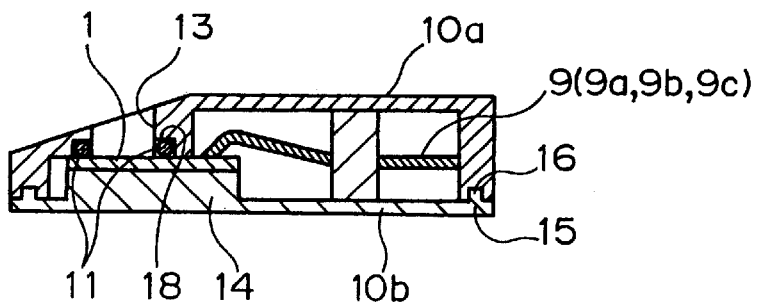
FIG. 6B is a cross-sectional view taken along the line VIB—VIB in FIG. 6A.

The cartridge 10 is comprised of an upper half 10a illustrated in FIGS. 4A, 4B, 7A and 7B, and a lower half 10b illustrated in FIGS. 5A and 5B.

As illustrated in FIGS. 4A and 4B, the operation electrode 4, the opposing electrode 5, and the reference electrode 6 of the urine sugar detecting sensor 1 are encased into the cartridge 10 so that they make contact with an external solution through a window 13 formed with the upper half 10a and that the leads 4b, 5b and 6b and the contact electrodes 4a, 5a and 6a do not make contact with an external solution. As explained later in detail, the contact electrodes 4a, 5a and 6a are designed to make electrical contact with a detecting circuit (not illustrated) mounted in the cartridge 10, through contact pins 9a, 9b and 9c.

As illustrated in FIGS. 5A and 5B, the lower half 10b of the cartridge 10 is formed with a raised base portion 14 on which the urine sugar sensor 1 is to be fixedly mounted. The lower half 10b is further formed at a periphery thereof with a projection 15 having a rectangular cross-section.

Figure 7A:
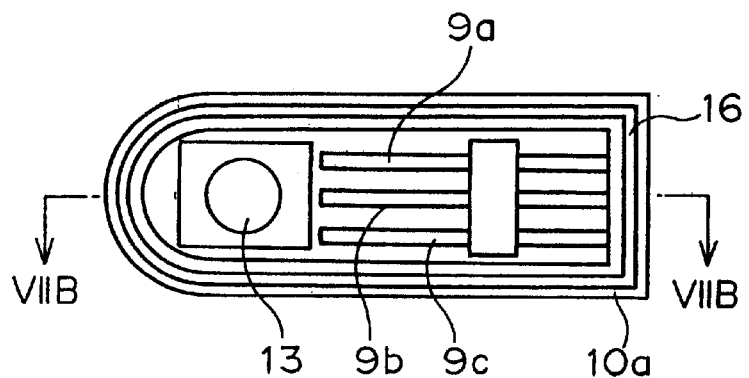
FIG. 7A is a plan view of an upper half of a cartridge constituting a urine sugar detecting sensor in accordance with the embodiment.
Figure 7B:
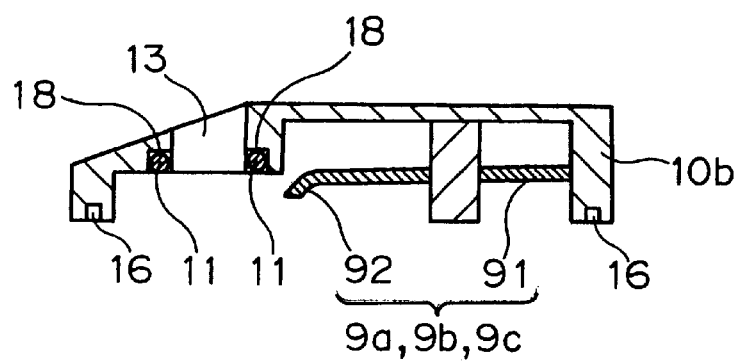
FIG. 7B is a cross-sectional view taken along the line VIIB—VIIB in FIG. 7A.

As illustrated in FIGS. 4A, 4B, 7A and 7B, the upper half 10a of the cartridge 10 is designed to be coupled to the lower half 10b to thereby form an enclosure. As best illustrated in FIG. 7B, the upper half 10a is formed with a peripheral lower surface thereof with a groove 16 having a rectangular crosssection, into which the projection 15 of the lower half 10b can be fit. The upper half 10a is formed with the window 13 above the raised base portion 14 of the lower half 10b. A wall defining the window 13 is formed at a lower surface thereof with a sealing groove 18.

As illustrated in FIG. 7A, the upper half 10a includes the contact pins 9a, 9b and 9c. Each of the contact pins 9a, 9b and 9c is comprised of a straightly extending proximal portion 91, and an obliquely, downwardly inclining distal portion 92. The proximal portions 91 are fixed to the upper half 10a, whereas the distal portions 92 are set free.

Each of the contact pins 9a, 9b and 9c are composed of phosphor bronze, and is plated with gold. Each of the contact pins 9a, 9b and 9c has a diameter of 0.45 mm and a length of 13 mm. The contact pins 9a, 9b and 9c are spaced away from one another in parallel by a distance of 1.27 mm, and the proximal portions 92 are integral with one another by resin.

Figure 8:
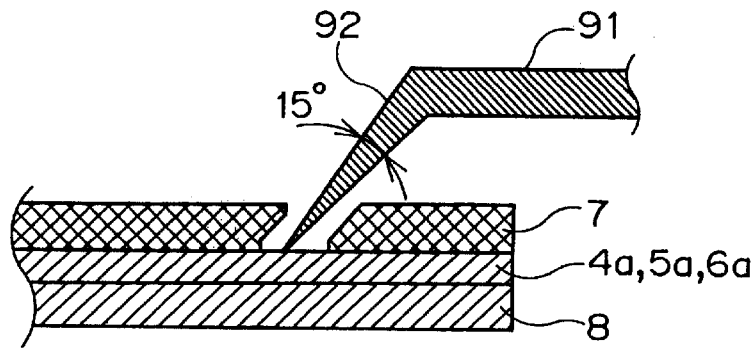
FIG. 8 is an enlarged view illustrating a contact pin and contact electrodes in a urine sugar detecting device in accordance with the embodiment.

The distal portion 92 of each of the contact pins 9a, 9b and 9c is 1 mm long, and inclines obliquely, downwardly by about 45 degrees. The distal portions 92 have a sharpened end having a point angle of 15 degrees. As illustrated in FIG. 8, the distal portions 92 pierce the glucose detecting film 7 to thereby make electrical contact with the contact electrodes 4a, 5a and 6a.

The upper and lower halves 10a and 10b are composed of ABS resin, and are designed to have a length 25 mm, a width of 12 mm, and a thickness of 0.5 mm. The coupled upper and lower halves 10a and 10b have a height of 5 mm.

A seal 11 is fit into the sealing groove 18 of the upper half 10a. The seal 11 is made from an acrylic adhesive sheet. The seal 11 is designed to have a size of 7 mm×7 mm and a thickness of 0.25 mm, and is formed centrally with an inner opening having a diameter of 4 mm. When the seal 11 is fit into the sealing groove 18, the inner opening of the seal 11 is in alignment with the window 13 having an inner diameter of 4 mm.

The urine sugar detecting device in accordance with the embodiment is assembled as follows.

First, the urine sugar detecting sensor 1 is fixedly adhered onto the raised base portion 14 of the lower half 10b.

Then, the contact pins 9a, 9b and 9c are mounted on the upper half 10a by inserting the contact pins 9a, 9b and 9c into positioning grooves (not illustrated). Then, silicone adhesive is applied to the groove 16 of the upper half 10a by means of a dispenser, and the seal 11 is fit into the sealing groove 18 of the upper half 10a.

Then, the projection 15 of the lower half 10b is fit into the groove 16 of the upper half 10a to thereby position the upper and lower halves 10a and 10b relative to each other, and the upper and lower halves 10a and 10b are adhered to each other through adhesive in fluid tight.

Thus, only the operation electrode 4, the opposing electrode 5, and the reference electrode 6 of the urine sugar detecting sensor 1 can make contact with external solution through the window 13 formed with the cartridge 10, and the leads 4b, 5b and 6b and the contact electrodes 4a, 5a and 6a are not allowed to make contact with external solution.

As illustrated in FIG. 8, when the upper and lower halves 10a and 10b are coupled to each other, since the contact pins 9a, 9b and 9c make contact with the urine sugar detecting sensor 1, the contact pins 9a, 9b and 9c are forced to be deformed. As a result, the distal portions 92 of the contact pins 9a, 9b and 9c receive a force generated due to the deformation of the contact pins 9a, 9b and 9c, and hence, pierce the glucose detecting film 7 formed on the contact electrodes 4a, 5a and 6a. Thus, the contact pins 9a, 9b and 9c make contact with the contact electrodes 4a, 5a and 6a, respectively, and thereby, make electrical contact with a detecting circuit (not illustrated) mounted in the cartridge 10.

The distal portions 92 of the contact pins 9a, 9b and 9c are designed to deform by such a length that they can pierce the glucose detecting film 7 by virtue of a force generated due to the deformation of the contact pins 9a, 9b and 9c. In this embodiment, the length is set about 2 mm.

Figure 9:
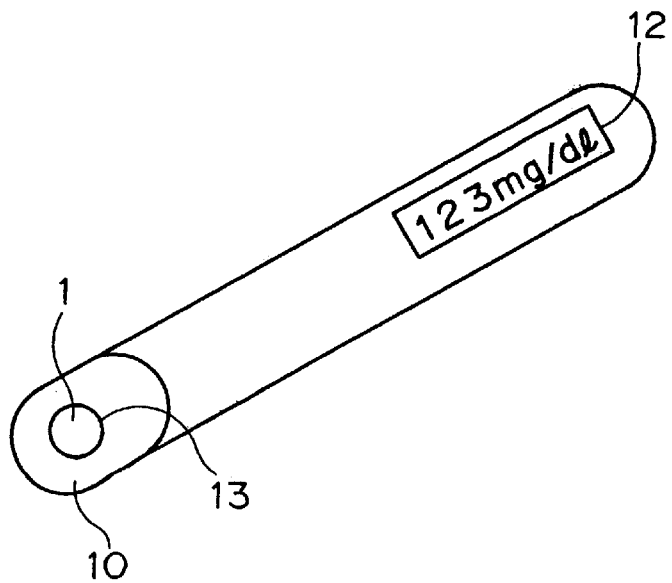
FIG. 9 is a perspective view illustrating a urine sugar detecting device in accordance with the embodiment.

FIG. 9 illustrates the urine sugar detecting device in accordance with the embodiment. Urine sugar is measured by dipping the urine sugar detecting device into urine. Enzymatic reaction occurs at a surface of the urine sugar detecting sensor 1 with the result of generation of hydrogen peroxide. The generation of hydrogen peroxide causes generation of an oxidation current, which is detected by the detecting circuit (not illustrated) mounted in the cartridge 10. The detecting circuit calculates a concentration of glucose, based on the thus detected oxidation current, and displays the calculated concentration in a display section 12.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The entire disclosure of Japanese Patent Application No. 10-072077 filed on Mar. 20, 1998 including specification, claims, drawings and summary is incorporated herein by reference in its entirety.

What is claimed is:

1. A urine sugar detecting device comprising:
   (a) a urine sugar sensor including at least one contact electrode and a cover film covering said contact electrode therewith;
   (b) a cartridge encasing said urine sugar sensor in fluid tight except said contact electrode; and
   (c) at least one contact pin encased in said cartridge and electrically connecting said contact electrode through said cover film.

2. The urine sugar detecting device as set forth in claim 1, wherein said contact pin pierces said cover film to thereby have electrical connection with said contact electrode.

3. The urine sugar detecting device as set forth in claim 1, wherein said contact pin is kept deformed in said cartridge so as to have a force with which said contact pin pierces said cover film.

4. The urine sugar detecting device as set forth in claim 1, wherein said contact pin is comprised of a straightly extending proximal portion and an obliquely, downwardly inclining distal portion.

5. The urine sugar detecting device as set forth in claim 4, wherein said distal portion inclines by about 45 degrees.

6. A method of fabricating a urine sugar detecting device, comprising the steps of:
   (a) fixing a urine sugar sensor in a lower half of a cartridge, said urine sugar sensor including a contact electrode and a cover film covering said contact electrode therewith;
   (b) fixing a contact pin in an upper half of a cartridge, said contact pin having a free distal end; and
   (c) coupling said lower and upper halves of a cartridge in fluid tight so that said distal end of said contact pin pierces said cover film, and makes electrical contact with said contact electrode.

7. A method of fabricating a urine sugar detecting device, comprising the steps of:
   (a) fixing a urine sugar sensor in a lower half of a cartridge, said sensor including a contact electrode and a cover film covering said contact electrode therewith;
   (b) fixing a contact pin in an upper half of a cartridge so that a straightly extending proximal portion of said contact pin is fixed and an obliquely, downwardly inclining distal portion of said contact pin is free; and
   (c) coupling said lower and upper halves of a cartridge in fluid tight so that said distal portion of said contact pin is deformed to thereby pierce said cover film, and makes electrical contact with said contact electrode.

8. The urine sugar detecting device of claim 1, wherein said cartridge comprises a lower cartridge half encasing said urine sugar sensor, and
   further comprising an upper cartridge half encasing said contact pin,
   wherein said lower cartridge half and said upper cartridge half are fluid-tight coupled.

* * * * *